United States Patent
Payton

(10) Patent No.: US 8,025,905 B2
(45) Date of Patent: Sep. 27, 2011

(54) METHOD FOR REDUCING ALLERGENCITY IN INDOOR SPACES

(76) Inventor: Hugh W. Payton, Naples, FL (US)

( * ) Notice: Subject to any disclaimer, the term of this patent is extended or adjusted under 35 U.S.C. 154(b) by 472 days.

(21) Appl. No.: 11/979,239

(22) Filed: Oct. 31, 2007

(65) Prior Publication Data

US 2008/0124297 A1    May 29, 2008

Related U.S. Application Data

(63) Continuation-in-part of application No. 11/529,586, filed on Sep. 29, 2006, now abandoned, which is a continuation-in-part of application No. 11/239,473, filed on Sep. 30, 2005, now abandoned, which is a continuation-in-part of application No. 10/153,612, filed on May 24, 2002, now abandoned.

(60) Provisional application No. 60/293,183, filed on May 25, 2001.

(51) Int. Cl.
*A61K 36/00* (2006.01)
*A61K 31/74* (2006.01)

(52) U.S. Cl. .................................. 424/725; 424/78.08
(58) Field of Classification Search .................. None
See application file for complete search history.

(56) References Cited

U.S. PATENT DOCUMENTS

| 6,830,764 B2 * | 12/2004 | Inui et al. ............ 424/669 |
| 2002/0040055 A1 * | 4/2002 | Inui et al. ............ 514/492 |
| 2002/0182184 A1 * | 12/2002 | Pearl et al. ............ 424/93.4 |

* cited by examiner

*Primary Examiner* — Christopher R Tate
*Assistant Examiner* — Randall Winston
(74) *Attorney, Agent, or Firm* — The Livingston Firm; Edward M. Livingston, Esq.; Bryan L. Loeffler, Esq.

(57) ABSTRACT

According to this invention, allergenicity in an indoor space is reduced by denaturing allergens in allergen reservoirs that are capable of producing respiratory or skin reactions and physically removing the allergens from the allergen reservoirs in the indoor space. The allergen reservoirs may also be treated with pesticides and fungicides/fungistats to prevent reinfestation of house dust mites, molds and cockroaches.

8 Claims, No Drawings

METHOD FOR REDUCING ALLERGENCITY IN INDOOR SPACES

CROSS-REFERENCE TO RELATED APPLICATIONS

This application is a continuation-in-part of Ser. No. 11/529,586 filed Sep. 29, 2006, which is a continuation-in-part of Ser. No. 11/239,473, filed Sep. 30, 2005, which is a continuation-in-part of U.S. application Ser. No. 10/153,612, filed May 24, 2002, which claims the benefit of U.S. Provisional Application No. 60/293,183, filed May 25, 2001. The aforementioned applications are hereby incorporated by reference in their entirety.

BACKGROUND OF THE INVENTION

1. Field of the Invention

This invention relates to medically sound procedures for reduction in environmental allergenicity due to certain airborne allergens known to produce asthma, allergic rhinitis and atopic eczema in both humans and animals. Specifically, allergens derived from house dust mites, certain molds, cockroaches, cats and dogs are removed from indoor living spaces to provide sanctuaries for asthma sufferers.

2. Review of Related Art

Asthmatic bronchitis (asthma), allergic rhinitis (hay fever), and atopic eczema are immunologic reactions which, in the majority of cases, are triggered by one or more allergens from five primary sources: cat dander, dog dander, mold spores, cockroach fecal pellets and house dust mite fecal pellets. All of the primary asthmatic allergens from these five sources are protein in nature, typically glycoprotein. These allergens accumulate on various indoor surfaces and in allergen reservoirs, such as carpets, upholstery, mattresses and pillows. The presence of these allergens in any interior space can make that space hazardous for an asthmatic patient.

Of the primary allergens, house dust mite (HDM) accounts for 50-55% of the asthmatic's problems. HDMs proliferate indoors when temperature, humidity and the presence of sloughed epithelial cells (the mite's primary food source) are adequate for their survival and reproduction. Adult HDMs produce 20-30 fecal pellets per day per mite over a life span of 2½ months. Each fecal pellet is heavily inoculated during its midgut formation with proteins (principally digestive enzymes) capable of evoking an immune response.

HDM allergenic proteins have been identified for mites of the genus *Dermatophagoides*, and the proteins fall mainly into two immunological groups: Der I (Der pI and Der fI) and Der II (Der pII and Der fII). The primary sequence of HDM allergens has been disclosed (see a series of U.S. patents and also reviews by Thomas, et al. (1998), "House-dust-mite allergens," *Allergy,* 1998 September; 53(9):821-32; Platts-Mills TA, et al. (1997), "Indoor allergens and asthma: report of the Third International Workshop," *J Allergy Clin Immunol* 1997 December; 100(6 Pt 1):S2-24; and Chua Ky., et al. (1996), "Analysis of sequence polymorphism of a major mite allergen, Der p 2," *Clin Exp Allergy.* 1996 July; 26(7):829-37). HDMs are primarily found in indoor textiles (carpet, upholstery, mattresses and pillows) where their population can become enormous—well into the millions. Mechanical disturbance can release the proteins from dried fecal pellets into the air, producing an allergenic cloud that will resettle onto textile surfaces over time.

Mold spores account for 10-15% of asthmatic reactions, and four mold genera account for nearly all of the allergenic spores. These genera are: *Alternaria, Cladiosporium, Aspergillus,* and *Penicillium,* with *Alternaria* accounting for about 80% of the mold spore responses of asthmatics. Cat dander accounts for 10-15%, cockroaches account for 5-10%, and dog dander accounts for 5-10% of asthmatic reactions.

HDM, cockroach and mold allergens tend to be larger and heavier; therefore, they often settle on textile-covered surfaces, such as carpets and upholstery. Even after being disrupted, such as when a person walks on a carpet or sits on a sofa, the allergens will only rise up a few feet in the air (e.g., about three feet) and quickly settle again.

Cat and dog allergens, on the other hand, tend to be smaller and lighter; thus, they often "float" in the air for up to six months. Eventually, those allergens will attach to a surface, such as a textile-covered surface, wall or ceiling. However, once they are disrupted, the allergens will again "float" in the air for a lengthy period of time before settling.

Physicians currently address the disorders produced by allergens with symptomatic medicinal approaches, desensitization methods and preventive measures such as textile removal from the home, air filters, dehumidifiers, mattress covers and the like, yet the problem still exists. Ablative HDM chemicals currently in use include short term insecticides or denaturants that reduce the allergenicity of protein allergens, such as the proteins in HDM fecal pellets. Insecticides that have been tested include benzyl benzoate (U.S. Pat. Nos. 5,916,917; 6,107,341; and 6,117,440) phenyl salicylate, the organophosphate, pirimiphos methyl (Mitchell, et al., 1985, "Reduction of house dust mite allergen levels in the home: uses of the acaricide, pirimiphos methyl," *Clin. Allergy,* 15:234), and synthetic pyrethroids such as permethrin (U.S. Pat. Nos. 5,843,981; 5,916,580; and 5,965,602; Glass, et al., "Evaluation of the acaricide permethrin against all stages of the American house dust mite *Dermatophagoides farinae* Hughes (Pyroglyphidae)," in Mitchell, et al., eds., *Acarology IX Proceedings,* Columbus, Ohio Biological Survey, 1997, pp. 693-695). International Publication No. WO 98/30236 discloses a pesticide using protease enzymes to kill insects for the purpose of decreasing or eliminating the incidence of allergic reaction to dust, but this reference does not address allergic reactions to the enzyme. Tannic acid has been used to denature HDM fecal pellets short term (Green, "Abolition of allergens by tannic acid," *Lancet,* 2:160 1984; U.S. Pat. No. 4,977,142), and polyphenol denaturants have been used in combination with insecticides (Green, et al., 1989, "Reduction of house dust mites and mite allergens: Effects of spraying carpets and blankets with Allersearch DMS, an acaricide combined with an allergen reducing agent," *Clin. Exp. Allergy,* 19:203; U.S. Pat. No. 4,806,526).

Either the insecticide treatments or the chemical denaturants must be reapplied at 2-3 month intervals for any hope of efficacy. These products are available over-the-counter, and are subject to the variability existing among do-it-yourselfers who apply such products. These products are also displaced from textiles during vacuuming and become air-borne, are inhaled, and can serve as a major irritant to asthmatics or hay fever sufferers. Therefore, there remains a need for improved methods of reducing allergenicity in indoor spaces to alleviate the suffering of asthmatics and hay fever sufferers.

SUMMARY OF THE INVENTION

It is an object of this invention to provide more effective methods for medically addressing asthma, allergic rhinitis and atopic eczema by creating "sanctuary" spaces with low allergenicity.

This invention provides methods for reducing allergenicity in an indoor space. In one embodiment, the method uses at least two of the following steps. One step provides for physically removing allergens capable of producing respiratory or skin reactions in asthmatics from allergen reservoirs in the indoor space. A second step provides for denaturing the allergens in the allergen reservoirs to reduce allergic reaction to the allergens. A third step provides for prophylactically preventing reinfestation of the indoor space by house dust mites and molds. In one exemplary embodiment, the step of physically removing allergen from allergen reservoirs is accomplished by vacuuming and hot water washing, the step of denaturing allergens is accomplished by enzymatic hydrolysis of the allergens and/or the step of preventing reinfestation is accomplished by treating allergen reservoirs with a pesticide plus a fungicide. In another exemplary embodiment, these steps are repeated periodically to maintain low levels of allergenicity.

In another embodiment, this invention provides a method for reducing allergenicity in an interior space comprising exposing textile-covered surfaces in an interior space to means for hydrolytically cleaving a plurality of peptide bonds in an allergenic polypeptide selected from the group consisting of house dust mite fecal antigens, cockroach fecal antigens, cat dander, dog dander and mold spores at ambient temperature, wherein the amount of active allergen in the interior space is consequently reduced. In one exemplary embodiment, said means for hydrolytically cleaving peptide bonds is a subtilisin-type protease, more preferably, the subtilisin-type protease is subtilisin savinase.

In yet another embodiment, this invention provides a method for reducing allergenicity in an interior space comprising treating textile-covered surfaces in the interior space with one or more proteolytic enzymes, wherein said one or more proteolytic enzymes cleave peptide bonds in allergenic polypeptides selected from the group consisting of house dust mite fecal antigens, cockroach fecal antigens, cat dander, dog dander and mold spores, and wherein allergenicity in the interior space is lowered. Typically, the textile-covered surface comprises a reservoir for the allergenic polypeptides, and the reservoir may comprise one or more of carpets, bedding, pillows or upholstery. Also, typically, the textile-covered surface is not immersed in water in the method of this invention and/or the textile-covered surface is incubated with the proteolytic enzyme under ambient conditions. In an exemplary embodiment, the proteolytic enzyme is applied to said textile-covered surface periodically, for example, semi-annually. In a another exemplary embodiment, the method of this invention further comprises at least one step selected from the group consisting of (a) vacuuming at least a portion of the allergenic polypeptide from the textile-covered surface and (b) washing the textile-covered surface with hot water to remove the allergenic polypeptide. In yet another exemplary embodiment, the one or more proteolytic enzymes are applied to said textile-covered surface in conjunction with a pesticide that limits house dust mite infestation, such as permethrin. In still another exemplary embodiment, the one or more proteolytic enzymes are subtilisin-type proteases. In even another exemplary embodiment, the enzyme is catalytically active at neutral pH.

In still another embodiment, this invention provides a method for reducing allergen load on an allergen reservoir comprising applying one or more proteolytic enzymes to the reservoir, wherein the one or more proteolytic enzymes cleave sufficient peptide bonds in allergenic polypeptides selected from the group consisting of house dust mite fecal antigens, cockroach fecal antigens, cat dander, dog dander and mold spores to reduce active allergen load in the reservoir. In one embodiment, the reservoir comprises animal fur and the one or more proteolytic enzymes are dispensed from a porous glove. Typically, the method of this invention is not carried out in a controlled reaction environment, but rather, the reaction conditions comprise ambient temperature. In a preferred embodiment, the one or more proteolytic enzymes are applied in conjunction with a pesticide. In an exemplary embodiment, the one or more proteolytic enzymes comprise a subtilisin-type protease, such as one that is catalytically active at a neutral pH. In another exemplary embodiment, the one or more proteolytic enzymes are applied contemporaneously with a pesticide and a fungicide. In a related embodiment, this invention provides an allergenicity-reducing composition comprising one or more proteolytic enzyme, a pesticide active against dust mites and a fungicide active against *Alternaria*.

In an additional embodiment, the method comprises denaturing, in allergen reservoirs, allergens that are capable of producing respiratory or skin reactions and physically removing the allergens from the allergen reservoirs in the indoor space. In one exemplary embodiment, the step of denaturing the allergens is accomplished by enzymatic hydrolysis of the allergens, the step of physically removing the allergens from the allergen reservoirs is accomplished by hot water washing and, optionally, vacuuming. In another exemplary embodiment, the method further comprises drying the allergen reservoir after the hot water washing. In yet another exemplary embodiment, the enzymatic hydrolysis is carried out by at least one proteolytic enzyme, optionally by two or more proteolytic enzymes. In still another exemplary embodiment, the at least one proteolytic enzyme is a subtilisin-type protease. The proteolytic enzyme may be incubated in ambient temperature for 1 to 30 minutes, such as 5 to 25 minutes or 10 to 20 minutes. The proteolytic enzyme may be catalytically active at neutral pH.

In any of the aforementioned embodiments, the method may further comprise deactivating the proteolytic enzyme, such as with an enzyme denaturant. In addition, the method may further comprise limiting the mobility, stabilizing, or physically restricting the movement of the enzyme in the environment through the addition of an adhesive. Enzyme denaturants that may be used include acetic acid, formic acid, sodium hypochlorite, hydrogen peroxide and/or citric acid, particularly citric acid. The methods may further comprise prophylactically preventing reinfestation of the indoor space by house dust mites and molds, such as by treating the allergen reservoirs with a pesticide, for example permethrin, and a fungicide. Moreover, in any of the aforementioned embodiments, the at least one proteolytic enzyme is delivered with an agglomerating agent, such as polyester, acrylic latex, polyvinyl acetate, solubilized starch, and polyvinyl alcohol (particularly polyvinyl alcohol). The allergens to be denatured in any of the embodiments are selected from the group consisting of house dust mite fecal antigens, cockroach fecal antigens, cat dander, dog dander and mold spores. The methods of the invention may be repeated periodically, such as annually. The allergen reservoirs of the aforementioned embodiments comprise textile-covered surfaces, such as carpets, bedding, pillows and upholstery, which may or may not be immersed in water.

In another embodiment of the invention, a method for reducing allergenicity in an indoor space comprises aerosolizing at least one proteolytic enzyme, optionally two or more proteolytic enzymes, in the indoor space, wherein said at least one proteolytic enzyme cleaves sufficient peptide bonds in allergenic polypeptides selected from the group consisting of house dust mite fecal antigens, cockroach fecal antigens, cat dander, dog dander and mold spores to reduce active allergen load in the indoor space. In an exemplary embodiment, the at lease one proteolytic enzyme is delivered with an agglomerating agent, for example, film-forming agents or glues, such as polyester dispersions, acrylic latex, polyvinyl acetate, solubilized starch, and polyvinyl alcohol, particularly polyvinyl alcohol. In another exemplary embodiment, the method may further comprise deactivating the proteolytic enzyme, such as with an enzyme denaturant, or limiting the mobility of the enzyme through the addition of an adhesive. Enzyme denaturants that may be used included acetic acid, formic acid, sodium hypochlorite, hydrogen peroxide and citric acid, particularly citric acid. In yet another exemplary embodiment, the method further comprises physically removing the allergenic polypeptides from allergen reservoirs in the indoor space by hot water washing, and optionally, vacuuming. The method may further comprise drying the allergen reservoirs after the hot water washing. In still another exemplary embodiment, the method further comprises prophylactically preventing reinfestation of the indoor space by house dust mites and molds, such as by treating the allergen reservoirs with a pesticide, for example permethrin, and a fungicide. In any of the aforementioned methods, the allergen reservoirs are incubated with the at least one proteolytic enzyme for 1 to 30 minutes, such as 5 to 25 minutes and 10 to 20 minutes. The at least one proteolytic enzyme may comprise a subtilisin-type protease and be catalytically active at neutral pH.

In one additional embodiment, a method for A method for reducing allergenicity in an indoor space comprises: applying at least one proteolytic enzyme to allergen reservoirs; incubating the at least one proteolytic enzyme at ambient temperature for 1 to 30 minutes; deactivating the proteolytic enzyme; physically removing the allergens from the allergen reservoirs; and treating the allergen reservoirs with a pesticide and a fungicide.

In another embodiment, this invention provides a method for reducing allergenicity in an interior space comprising exposing textile-covered surfaces in an interior space to negatively charged polymers such as the film-forming polymers or glues described above. Such polymers include polyester dispersions, acrylic latex, polyvinyl acetate, solubilized starch, and polyvinyl alcohol, particularly polyvinyl alcohol. Additionally, the negatively charged polymers include natural and synthetic absorbent polymers, e.g., natural cellulosic polymers such as carboxymethylcellulose nitrate and synthetic polymer such as acrylic acid polymers. Preferably, the polymers are applied in conjunction with an antimicrobial or antifungal agent.

In another embodiment, this invention provides a method for reducing allergenicity in an interior space comprising coating or impregnating an air filter matrix with negatively charged polymers and allowing the air to pass through the coated or impregnated air filter matrix, thus removing the allergens from the air. The polymers include the film-forming polymers or glues described above and include polyester dispersions, acrylic latex, polyvinyl acetate, solubilized starch, and polyvinyl alcohol, particularly polyvinyl alcohol. Additionally, the negatively charged polymers include natural and synthetic absorbent polymers, e.g., natural cellulosic polymers such as carboxymethylcellulose nitrate and synthetic polymer such as acrylic acid polymers. In this embodiment, the coated or impregnated matrix may be periodically moistened so as to maintain the anionic nature of the polymers. Preferably, the polymers are applied in conjunction with an antimicrobial or antifungal agent.

In another embodiment of the invention, a method for reducing allergenicity in an indoor space comprises aerosolizing negatively charged polymers, such as the film-forming polymers or glues described above. Such polymers include polyester dispersions, acrylic latex, polyvinyl acetate, solubilized starch, and polyvinyl alcohol, particularly polyvinyl alcohol. Additionally, the negatively charged polymers include natural and synthetic absorbent polymers, e.g., natural cellulosic polymers such as carboxymethylcellulose nitrate and synthetic polymer such as acrylic acid polymers. Preferably, the polymers are applied in conjunction with an antimicrobial or antifungal agent.

In yet another exemplary embodiment, the method further comprises physically removing the allergen from allergen reservoirs in the indoor space by hot water washing, and optionally, vacuuming. The method may further comprise drying the allergen reservoirs after the hot water washing.

DETAILED DESCRIPTION OF EMBODIMENTS OF THE INVENTION

This invention relates to medical and veterinary medicine procedures addressing certain allergens known to produce asthma, allergic rhinitis and atopic eczema in both humans and animals. The specific allergens are derived from house dust mites, certain molds, cockroaches, cats and dogs. These allergens are proteins, typically complex glycoproteins, having polypeptide structures which render the molecule allergenic.

The goal of this invention is to offer the immunologically compromised patient an organized, professional and holistic approach to control the major indoor antigens (derived from HDM, molds, cockroach, cat and dog) that are capable of producing the medical conditions asthmatic bronchitis, allergic rhinitis and atopic eczema. The major habitat for these antigens is textiles which provide adequate humidity, temperature and food for proliferation of the sources of these allergenic antigens. Antigen prevention should address temperature, humidity and food, but taken individually or collectively, simply addressing these factors in any combination is grossly inadequate to decrease antigen levels below established medical statistical antigen levels capable of inciting allergic response in a sensitized individual.

Within the indoor environment, the primary asthmatic allergens are commonly found in allergen reservoirs, such as textiles (carpet, upholstery, mattresses, pillows, etc.). According to this invention, allergenicity in an indoor space is reduced by denaturing allergens in allergen reservoirs that are capable of producing respiratory or skin reactions and physically removing the allergens from the allergen reservoirs in the indoor space. The allergen reservoirs may also be treated with pesticides and fungicides/fungistats to prevent reinfestation of house dust mites, molds and cockroaches.

DEFINITIONS

For the purpose of describing the present invention, the following terms are defined.

"Indoor space" means an enclosed space containing a body of air for which passage of air into and out of the space is hindered (e.g., by solid walls, semi-permeable screens, doors, windows, etc.), so that particulates or aerosols suspended in the atmosphere of the indoor space will dissipate only slowly by settling or exchange with the atmosphere in adjacent spaces through limited connecting passages (e.g., through doors and windows or by diffusion through screens). Examples of indoor spaces include the interior of a residential dwelling, a room or suite of rooms that is not subject to free exchange of air with the outdoors, the inside of airplanes, buses, automobiles, trains, hotel rooms, offices, assembly or meeting halls, etc.

"Primary allergens" as discussed herein are allergens found in cat dander, dog dander, mold spores, cockroach fecal pellets and house dust mite fecal pellets that are associated with asthma, allergic rhinitis and atopic eczema in both humans and animals.

"Allergen reservoir" means any region or volume in an indoor space that can dispense allergens when mechanically disturbed. Typical reservoirs are woven materials including textiles such as carpets, upholstery, pillows and bedding or baskets and mats. Allergens may accumulate in the reservoirs by settling from an allergen aerosol or by deposition from an infestation of insects of other sources of allergens.

"Active allergens" are chemical entities, typically macromolecules, that cause an allergic reaction in a sensitized individual. If the chemical entities are chemically modified so that they no longer cause the allergic reaction, the entities have become inactive allergens. The allergenic effect is typically caused by binding of regions on the macromolecular allergen to receptors in the sensitized individual. These regions are called epitopes, and modification of the epitopes can result in inactive allergens.

"Allergen load" means the level of active allergen in some volume or area, which may be an indoor space or an allergen reservoir. Typically, allergen load is measured by collecting the allergen in some volume or area (e.g., by filtering allergen from an aerosol or by mechanically disturbing an allergen reservoir and collecting the allergen released) and measuring the amount of allergen, for example by ELISA.

To "lower allergenicity" means reducing the allergen load in the designated space or reservoir. Target allergen level for house dust mite allergen is less than 2 micrograms/gram dust; levels above 10 micrograms/gram dust are likely to produce some symptoms in mite-sensitive asthmatics, and 100 micrograms/gram dust is likely to provoke an asthma attack. While it is preferred to reduce HDM allergen levels to below 100 micrograms/gram dust or lower, any reduction of the allergen level is beneficial to allergy sufferers. Indeed, the amount of relief an allergy sufferer experiences is directly proportional to the reduction in allergen level. Thus, reducing the allergen level by 10% may provide approximately 10% of relief. Although a 100% reduction in allergenicity is optimum, a reduction of allergenicity in a designated space or reservoir of at least 30% is a significant benefit to allergy sufferers.

"Ambient conditions" refers to conditions that will affect the rate of chemical reactions, such as temperature, pressure, etc., as those conditions exist normally in contrast to controlled conditions which occur inside closed vessels and consciously deviate from ambient to facilitate some action. Ambient conditions exist, for example, in a bedroom or a garden, while controlled conditions exist inside a refrigerator or a washing machine or a chemical reactor.

Proteases are enzymes which catalyze the hydrolysis of polypeptides to produce peptide fragments. The polypeptides consist of various different amino acid residues connected by peptide bonds, and proteases may catalyze hydrolysis of bonds between certain amino acid residues in preference to other peptide bonds. "Subtilisin-type proteases" are peptide-hydrolyzing enzymes equivalent to the proteases secreted by various species of *Bacillus*. The proteases from *Bacillus* species are relatively non-selective among the various peptide bonds. In particular, subtilisin savinase, derived from *Bacillus lentus*, and subtilisin BPN, derived from *B. amyloliquefaciens* have been shown to be effective.

Physical Removal of Allergens

Studies have shown that dry vacuum can remove up to 50-55% of the house dust mite material from allergen reservoirs, such as carpets. Effectiveness of the vacuum protocol may be confirmed by ELISA (see, e.g., Example 2, below). As an example, a portion of carpet might by divided into two test plots, and each extracted with hot water, after one of the plots had been vacuumed. The effectiveness of the vacuum may be determined by comparing the amount of HDM substance in the two extracts by ELISA. Procedures for measuring the allergen level in an environmental area are also disclosed in U.S. Pat. No. 5,679,535, which is incorporated herein by reference, and the skilled artisan will be able to develop variant methods from the description therein.

Even more effective allergen removal from allergen reservoirs can be achieved by hot water washing, such as extraction. The hot water typically used on an allergen reservoir is from 120° F. to 160° F., depending on the equipment used. In one embodiment, the hot water includes surfactants to facilitate mobilizing the allergenic material from the textile fibers. Such a procedure has been shown to remove substantially all of the allergens (<2 microgram of the house dust mite substance/gram dust). Effectiveness of the hot water wash and/or extraction may also be confirmed by ELISA as described above.

In one exemplary embodiment of the invention, water at a temperature of 120-140° F. is applied to a textile-covered surface, such as a carpet, followed promptly by vacuum removal of as much of the water as possible (typically 95%). In another exemplary embodiment, the textile-covered surface is washed and then, after removal of most of the water, the surface is dried with a dryer, such as a high-power industrial fan. Removal of water and/or drying is important for the prevention of mold overgrowth.

The hot water wash may occur before, during or after the degradation of allergens, or any combination thereof. For example, the allergen reservoir may be washed, and then a solution comprising the allergen denaturant, such as a hydrolyzing enzyme, may be applied. In another example, the allergen denaturant may be in the wash solution. As another example, the allergen reservoir may be washed after degradation of the allergens, and the wash solution may comprise an enzyme deactivator.

Enzymatic Degradation of Allergens

As discussed above, the primary asthmatic allergens are glycoproteins. Proteases (which may be genetically engineered) are capable of catalyzing the hydrolytic cleavage of these listed allergenic glycoproteins into peptide fragments, thereby denaturing their allergenicity. The proteolytic fragments are both less allergenic and more easily mobilized from the textile during the physical removal process. Therefore treatment with enzymes further reduces the allergenicity associated with treated textiles. Surprisingly, the fragments do not form highly allergenic aerosols.

Any enzyme that will cleave the allergenic polypeptides to destroy the epitopes recognized by the asthmatic's sensitized immune system is suitable, but proteases that are less specific (i.e., hydrolyze peptide bonds between a variety of different amino acid residues, rather than only between specific residues) are preferred. In particular, subtilisin-type proteases from various *Bacillus* sp. have been shown to be effective, including subtilisin savinase, derived from *Bacillus lentus*, or subtilisin BPN, derived from *B. amyloliquefaciens*. Similar non-specific proteases are suitable for use in this invention, as well as *Bacillus* neutral proteases and the like. Genetically engineered enzymes are within the contemplation of this invention, so long as the resulting enzyme can be shown to destroy allergenic epitopes of the primary allergens, as shown by ELISA tests (see, e.g., U.S. Pat. No. 5,314,991). Suitable assays may be analogous to the tests for active T cell epitopes of Der pI, Der pII, Der $f_1$, and Der fII disclosed in U.S. Pat. No. 5,968,526 (incorporated herein by reference).

Application of the enzymes to the textile may be by any suitable procedure. The enzymes may be applied in a separate step, with the hot water used for physical removal, or with the prophylactic pesticide/fungicide discussed below. Typical formulations will be buffered to avoid extremes of pH that are detrimental to enzyme stability, and may include other well known enzyme stabilizers, such as polyols, calcium salts or other ionic stabilizers.

Since allergens may become airborne when the allergen reservoir is disturbed and some may even "float" for a lengthy period of time, it is advantageous, in some cases, to deliver the enzyme with an agglomerating agent. When the enzyme is aerosolized, agglomeration occurs due to the concentration of solutes as the water evaporates. The agglomerating agent will not only help to attract an allergen to the enzyme, but it will also help to weigh down the allergen so that it will settle out of the air more quickly. Moreover, the large size of the enzyme/agglomerant molecule will help inhibit inhalation into the lungs. Agglomerating agents that may be used include polyester, acrylic latex, polyvinyl acetate, solubilized starch or polyvinyl alcohol (PVA).

In a particular mode, an aqueous solution of the enzyme is absorbed in a porous matrix that is then run over the allergen reservoir to be treated, and the enzyme solution is dispensed into the reservoir by capillary action. One example of such a porous matrix is a sheet of sponge-like material incorporated into the palm of a glove that is worn by a person when petting a cat or dog. The enzyme solution is applied to the animal's coat from the sponge, and the solution will penetrate the coat to the animal's skin (adjacent to sebaceous glands) to degrade all or a portion of the allergenic antigen in the fur reservoir (especially cat dander antigen). This method is particularly useful as part of the veterinary treatment of asthmatic pets discussed in more detail below.

In another embodiment of the invention, the enzyme solution is delivered via aerosol or fogger (collectively referred to as "aerosolized enzyme"). The enzyme solution may be aerosolized through use of, e.g., a total release canister or a spray gun. The aerosolized enzyme would allow the enzyme to come in to contact with the smaller and lighter allergens, such as those from cat and dog dander, that are "floating" in the air. In one exemplary embodiment, the enzyme is delivered with an agglomerating agent as described above so that the allergen will "stick" to the enzyme/agglomerant molecule. This will not only provide for the attraction of the allergen to the enzyme, but it will also provide the needed weight for the allergen to settle out of the air.

In another exemplary embodiment, the aerosolized enzyme is negatively charged, such as through an electrostatic filter or other methods known in the art, so that the enzyme molecule will attract allergens, which are positively charged. The aerosolized enzyme may optionally contain stabilizing agents to enhance durability (e.g. of the enzyme or the aerosol). In one embodiment, the negatively charged aerosolized enzyme is delivered with an agglomerating agent as previously described.

Controlling the Allergenicity of the Degrading Enzyme

It is well known that high concentrations of enzymes may cause allergic reactions. Therefore, it is recommended that the enzyme concentration on an indoor surface be less than 65 µg/m².

To address this issue, one embodiment of the invention provides a method that further comprises deactivating the enzyme after hydrolysis has occurred. In one exemplary embodiment, the enzyme is deactivated by using an enzyme denaturing agent, such as acetic acid, formic acid, sodium hypochlorite, hydrogen peroxide or citric acid. In an exemplary embodiment, the enzyme denaturant is an acidic solution, such as 0.5-5.0% citric acid solution.

In one embodiment of the invention, the enzyme denaturant is applied before the physical removal of the allergen. In another embodiment, the enzyme denaturant is applied with the hot water washing solution used to physically remove the allergen. In yet another embodiment, the enzyme denaturant is applied after the physical removal of substantial portions of the allergen.

In an exemplary embodiment of the invention, at least one proteolytic enzyme, such as a subtilisin-type protease, is applied to the allergen reservoir; incubated at ambient temperature for 1 to 30 minutes, for instance 10-20 minutes, and deactivated with an enzyme denaturant, such as an acidic solution. Then, the allergens are physically removed the from the allergen reservoir, for example, by hot water washing, which is followed by drying. Finally, the allergen reservoir is treated prophylactically, such as with a pesticide and a fungicide as described below.

Another embodiment that may be used to prevent allergic reactions to the proteolytic enzyme comprises the addition of an adhesive to the formulation containing the enzyme, so that when the composition is applied and dries, the adhesive adheres the enzyme to the applied surface. When the enzyme is adhered to the surface, allergic reactions to the enzyme may be prevented as the enzyme is no longer able to become airborne and is in effect sequestered on the surface. The adhesives are a subset of the aforementioned agglomerating agents that are capable of imparting adhesion and include polyester such as polyester dispersions, acrylic latex, polyvinyl alcohol, polyvinyl acetate, starch or combinations thereof. The adhesives may also be selected to impart a desired degree of flexibility when dried. The particular adhesive polymers useful in the present embodiment are known to one of ordinary skill in the art and may be selected to impart the desired degree of adhesiveness and flexibility described above.

According to a preferred embodiment, the adhesive acts as a binder and in the liquid state allows the enzyme to agglomerate, thus weighing down the enzyme. As the treatment dries, the adhesive anchors the enzyme to the surface.

When the enzyme is applied in combination with an adhesive, the adhesive imparts a degree of safety to the composition in that the enzyme is no longer free to move about within the environment. Because of the reduced mobility of the enzyme, allergic reactions that may result due to the presence of the enzyme are reduced or eliminated.

The enzyme and adhesive may be applied to any surface including, but not limited to: textiles, such as carpet; filters, such as air filters; or any other surface that requires treatment against allergens.

In another embodiment, the enzyme may be used in a waste treatment composition, for example to treat odors in clay (e.g., kitty litter). In this embodiment, the adhesive adheres the enzyme to clay in the dry state. When the clay is wetted, the enzyme is released, exhibiting the desired waste treatment activity. Upon drying, the enzyme is re-anchored to the clay surface. The enzyme and adhesive may be added to clay compositions in a manner known to one of ordinary skill in the art, such as the methods set forth in U.S. Pat. Nos. 5,634,431 and 6,207,143, which are herein incorporated by reference in their entirety.

Agglomeration of Allergen Through Treatment with Anionic Polymers

The negatively charged polymers will attract allergens that are positively charged. The polymers therefore act to remove such allergens from the environment through agglomeration of the allergen and polymer as a result of this ionic interaction. The allergen/polymer agglomerated complexes that are formed can then be removed from the treated area as described below or allowed to remain in the treated area, with the allergen sequestered in the complex. Suitable negatively charged polymers include polyester, acrylic latex, polyvinyl acetate, solubilized starch or polyvinyl alcohol (PVA). As described above, such negatively charged polymers are preferably adhesive in nature, and thus will bond to surfaces to which they are applied, e.g., textiles and air filter matrices. Additionally, the negatively charged polymers include natural and synthetic absorbent polymers, e.g., natural cellulosic polymers such as carboxymethylcellulose nitrate and synthetic polymer such as acrylic acid polymers. Preferably, the polymers are applied in conjunction with an antimicrobial or antifungal agent. Applications of the negatively charged polymers to suitable surfaces are described below.

Application of the negatively charged polymers to a textile may be by any suitable procedure. The negatively charged polymers may be applied in a separate step, with the hot water used for physical removal, or with the prophylactic pesticide/fungicide discussed below.

Coating or impregnating of the negatively charged polymer to an air filter matrix may be made by any known procedure, including, e.g., spray coating. In one such procedure, a polymer latex may be spray coated onto and allowed to penetrate into a filter matrix. In order to maintain the ionic nature of the polymers, the filter matrix typically is periodically rewetted, e.g. through spraying the coated or impregnated filter matrix with water. Various air filtration media are well known, for example those in HVAC systems having matrices which include, but are not limited to fiberglass and fibrous webs of addition polymers, e.g., polypropylene fibers.

In a particular mode, an aqueous solution of the polymer is absorbed in a porous matrix that is then run over the allergen reservoir to be treated, and the polymer solution is dispensed into the reservoir by capillary action. One example of such a porous matrix is a sheet of sponge-like material incorporated into the palm of a glove that is worn by a person when petting a cat or dog. The polymer solution is applied to the animal's coat from the sponge, and the solution will penetrate the coat to the animal's skin (adjacent to sebaceous glands). This method is particularly useful as part of the veterinary treatment of asthmatic pets discussed in more detail below.

In another embodiment of the invention, the polymer solution is delivered via aerosol or fogger (collectively referred to as "aerosolized polymer"). The enzyme may be aerosolized through use of, e.g., a total release canister or a spray gun. The aerosolized polymer would allow the polymer to come into contact with the smaller and lighter allergens, such as those from cat and dog dander, that are "floating" in the air. In one exemplary embodiment, the allergen will "stick" to the polymer molecule. This will provide the needed weight for the allergen to settle out of the air, as well as allowing the allergen to be sequestered in the complex as described above.

Prophylactic Treatment

House dust mites and mold spores are ecologically interlocked. Mold spores are the principal diet of immature dust mites. Furthermore, mold spores settle on sloughed epithelial cells which form the principal food source for adult dust mites, and mold secretes enzymes that predigest the epithelial cell proteins to make them more easily assimilated by the mites. Thus, reducing mold spore levels will have a limiting effect on mite infestation. Together, HDM and mold spores account for about two-thirds of the asthmatic's problems, so restraining the reaccumulation of these two allergens will provide significant relief for the asthma sufferer.

Application of a pesticide targeted at mites and a microbicide/stat targeted at the allergenic molds can maintain the low level of allergenicity achieved by physical cleaning and/or enzymatic degradation of the allergens in a target area. Pesticides that have some effect against dust mites are known, and use of such pesticides is within the contemplation of this invention. Pesticides that are effective against both house dust mites and cockroaches may be used, but even more preferred are pesticides of extremely low human toxicity that are effective against the major allergen-producer—house dust mites.

Permethrin is a synthetic pyrethroid that is less toxic to humans than most other pyrethroid derivatives. Permethrin is currently used for treating head lice and scabies; an ointment containing 5% permethrin is applied for 12 hours, then washed off. Less than 2% of the permethrin is absorbed through the skin. Permethrin is a particularly preferred pesticide for use in the methods of this invention since it can achieve 100% kill of house dust mites in carpet at levels of only 0.1% permethrin. Another class of suitable pesticides are polyheterocyclic compounds, such as ivermectin, avermectin or abamectin (collectively referred to as "Avermectins"). Avermectins are typically applied to control mites on foliage or fruit at about 0.014%. Avermectins may be used at concentrations of less than 0.014% for carpets.

As discussed above, application of pesticide is likely to be more effective if it is accompanied by an antimicrobial compound effective as a fungicide or fungistat. (The term "fungicide" will be used hereinafter to represent either fungicides or fungistats, or combinations thereof.) In particular, fungicides should be chosen for their effectiveness against the four mold genera responsible for asthma-inducing allergens: *Alternaria, Cladiosporium, Aspergillus*, and *Penicillium*, most particularly *Alternaria*. The skilled artisan will be aware of suitable tests for fungicidal efficacy, including inhibition of fungal growth in petri dishes or shake flask cultures. Preferably, the antimicrobial compound selected as fungicide according to this invention will be stable when formulated under conditions suitable for permethrin. Organophosphate 2-ethylhexyl esters (antimicrobial chemicals sold under the trademark INTERSEPT) are suitable, as is asoxystrobin. Other antimicrobials meeting the criteria provided herein may be selected by the skilled worker.

Typically, the pesticide and fungicide are formulated in an aqueous mixture or in other volatile solvent(s) for application to the textiles that might serve as allergen reservoirs. The mixture may be sprayed onto the textiles or painted on or applied by any other method that provides a relatively even coating throughout the body of the textile. Application methods also include padding, sponging, foaming, e.g., aerosol and spraying (e.g., power and pump). The solvent will volatilize, leaving a residue of pesticide and fungicide to serve to inhibit development of new mite infestations and/or mold inoculation of the textile material. The presence of the pesticide/fungicide will postpone the need for repeat cleaning to maintain low allergen load in the indoor space occupied by the textiles. Preferably, the pesticide and the fungicide are chosen to retain efficacy as applied for substantially similar periods. Most preferably, both the pesticide and the fungicide as applied will retain efficacy for at least six months or even for over a year.

Prophylactic compositions containing permethrin and asoxystrobin are of particular interest because both of these agents migrate into textile fibers where they are ionically bound, resulting in extended periods of efficacy and reduced volatility for lower toxicity and allergenicity of the prophylactic agents. Another desirable formulation is an aerosol that can deposit active components in the same reservoir areas reached by cat dander allergen, including light fixtures, ceiling fans, cabinet tops, etc. Application of the prophylactic compositions in heating or air conditioning ducts, either as aerosols or by impregnating air filter matrices in the ducts, is also within the contemplation of this invention.

Veterinary Treatment

Animals are also susceptible to allergic asthmatic reaction against the same allergens that affect humans, particularly HDM. In particular, asthma has been diagnosed in household pets, such as cats and dogs. Allergen reservoirs associated with animal asthma include the animal's coat, pet beds or sleeping mats, and litter boxes. In addition to treatment to apply enzymes to an animal's coat with a porous glove as described above, animal asthma may be treated by applying enzymes to the textiles in pet beds or a pesticide/fungicide combination to either pet bed textiles or to the animal's coat. Enzymes and/or pesticide/fungicide combinations may also be added to the pet's bath water or dispersed in an indoor space by aerosol bomb. To prevent allergic reactions (either in the pet or in the owner) from the enzyme, the enzyme may be deactivated, for example with an enzyme denaturant. Alternatively, or in addition to the enzyme deactivation, the allergen reservoir may be washed with hot water.

EXAMPLES

In order to facilitate a more complete understanding of the invention, Examples are provided below. However, the scope of the invention is not limited to specific embodiments disclosed in these Examples, which are for purposes of illustration only.

Example 1

Allergen Control System

Major university laboratory and double-blinded clinical studies have proven the following indoor textile "cradle to grave" holistic approach to be capable of maintaining HDM and HDM fecal pellet antigens below levels capable of producing allergenic response (2 microgram HDM antigen per gram of dust):

Phase One

Ideally carpet, upholstery and bedding should be anti-antigen treated during manufacturing bilaterally with SMITE™, i.e., synthetic permethrin, and UNISEPT™ i.e., fungistat/fungicide[1]. HDM antigen is the major indoor antigen (55%) which coexists with mold antigen (10-15% of indoor antigen load). There is synergism between HDMs and mold spores in that:

[1] Phosphoric acid, bis(2-ethylhexyl) ester, compd.

a) Immature HDMs food source consists of mold spores
b) Mold spores predigest epithelial cells which is the major food source of adult HDMs.

Accordingly new textile products for indoors that are involved in this issue should be prophylactically controlled against both HDMs and mold. Fungistats/fungicides must be specific in addressing the four molds that are predominate in creating immunological response (*Alternaria* 80%), *Cladosporium, Penicillium, Aspergillus*)

Phase Two

A. New products containing SMITE™ and UNISEPT™ deteriorate over time necessitating re-application of the acaricide and fungicide at intervals of one year. The textile product must be dry vacuumed, then subjected to hot water extraction for dirt, dust, HDMs, mold spores and other antigens prior to applying the pesticides. Hot water extraction obviously leaves moisture residual which translates into mold overgrowth and proliferation, thereby necessitating application of UNISEPT™ along with the acaricide SMITE™.

B. In-Use Products (textiles)—mite/mold infested: Priority-wise, the highest concentration of HDMs exists in mattresses and pillows followed by upholstery. The greatest numbers of HDMs exists in carpet. Thusly, in-use textiles that are a habitat for mites and mold should likewise be:

a) Professionally vacuumed (dry) which will remove 50% of dust, dirt, HDMs, mold spores and other antigens in carpet as proven in our laboratories.
b) Followed by professionally hot water extraction which will remove 100% of the HDM antigen, as laboratory tests have proven.
c) Followed by professional application of SMITE™ and UNISEPT™. Professional applicators will apply these pesticides with a special nozzle to insure:
Even distribution of the chemicals to textiles to control mite and mold regrowth for one year after antigen removal
This specialized nozzle will also assure even in-depth penetration of chemicals for HDMs, which, although blind, abhor light and accordingly are embedded in textiles well below the surface.
d) Professional drying procedures are practiced to inhibit mold overgrowth.

These in-use textile procedures should be duplicated at approximately one year intervals for maximum antigen protection even though:

a) SMIE™ will control 85% of the HDM population for one year before declining slowly to 52% HDM control and 48 months.
b) UNISEPT™ is near 100% effective against all immunologically significant molds for one year.

Both SMITE™ and UNISEPT™ are EPA registered for these specific goals, are water miscible, user friendly toxicity-wise, basically nondisplacable, low volatility, odorless, dye and fabric friendly.

Phase Three

The major antigens this invention addresses emanate from HDMs, mold spores, cockroaches, cat and dog. All of these antigens are allergens composed of glycoproteins at the molecular level. The antigenicity of the allergen is manifested via the amino acid radicals comprising the complex glycoprotein. The inventor has proven that the HDM antigen can be completely denatured of all activity immunologically with the use of genetically engineered enzymes called proteases. Protease can be specific for proteins, carbohydrates or fats in disassembling their specific molecules, or a combination of proteases can be used to denature and fragmentize complex glycoproteins. The resultant fragments are non-allergenic.

Application methodology of proteases to denature the antigens of HDMs, mold, cockroach, cat and dog herein discussed would include:

Protease use with detergents to clean textiles infested with antigens.

Impregnate heating/AC filters with proteases.

Aerosol bombing of areas infested with antigens

Pet usage: Proteases on grooming tools, in bath water, in litter boxes, in sleeping mats, etc.

Example 2

Measurement of Allergen Load

Allergen load in carpet is measured by vacuuming a measured square yard of carpet with a hand-held vacuum, having a dust collecting bag, by stroking for 30 seconds in each of two perpendicular directions. The allergen content is determined by ELISA measurement normalized per gram of collected dust.

IMMULON™ microtiter plates are bound with monoclonal antibodies (mAb) specific for individual antigens. After washing plates with phosphate-buffered-saline (PBS) 2×, the plates are saturated with 100 microliters of 1% bovine serum albumin in PBS. Next 100 microliter of doubling serial dilutions from 250 ng/mL to 0.5 ng/mL of reference allergen standard of pre-set dilutions of samples are added and allowed to incubate for one hour. Following incubation, plates are washed 5× with PBS and wells are coated with biotinylated specific mAb and allowed to incubate, then washed and coated with streptavidin-peroxidase solution. Bound biotinylated-labeled antibody is detected by using 2',2'-azino-bis(3-ethyl-benzthiazoline)sulfonic acid as a chromogen and $H_2O_2$ as a substrate. Each plate will be read when the optical density of the highest standard reaches 2.2 using a DYNATECH™ microplate spectrophotometer at 405 nm. Level of active allergen in each sample will be determined by interpolation from the reference curves and reported in microgram antigen/gram dust.

Example 3

Efficacy of Allergen Denaturant on HDM, Cockroach, and Dog Allergens

Eight different Allergen Denaturant solutions were prepared using four different subtilisin-type proteases and two different binding agents [AD1-AD4 had UNIBOND 1808, which contains water-dispersible polyester resin, and AD5-AD8 had UNIBOND 1809, which contains solubilized polyvinyl alcohol (both binding agents are from Unichem, Inc., Haw River, N.C.)]. Each solution was tested against a standard to ensure that the Allergen Denaturant solutions did not interfere with commercially available mAb ELISA tests (INDOOR Biotechnologies, Inc., Charlottesville, Va.) used to measure exposure to allergens. Detection was performed by using a POWERWAVE 200 (Biotek Instruments, Inc., Winooski, Vt.). The test showed that the Allergen Denaturant solutions did not interfere with the ELISA system.

The Allergen Denaturant solutions were then tested with Der p 2 mite allergen, Can f 1 dog allergen and Bla g 2 cockroach allergen. First, the ELISA plates were coated with anti-Der p 2 mAb 1D8, anti-Can f 1 mAb 6E9 and anti Bla g 2 mAb 7C11 overnight at 4° C. The three allergens were incubated with the eight Allergen Denaturant solutions and a PBS control, for a total of 27 samples, and incubated for two hours at room temperature.

After incubation, the samples were diluted 1/100, 1/200, 1/400 and 1/800 and tested with the commercial ELISA kits and detected as described above. Curves of the four dilutions for each sample were generated and compared to the standard curve. An average of the 4 dilutions, as determined by the standard curve, was calculated to determine the concentration of allergen remaining after exposure to the Allergen Denaturant solutions. The effect of the Allergen Denaturant solutions were expressed as a percent reduction of the allergen concentration after exposure to the solutions compared to the concentration of the allergen without an Allergen Denaturant solution (PBS Control). Results of the tests are shown below in Tables 1 to 3 below.

TABLE 1

Efficacy of Allergen Denaturant Solutions on Mite Allergen

| Allergen Denaturant Solution | Der p 2 (μg/ml) | % Reduction Der p 2 |
|---|---|---|
| PBS Control | 322.5 | |
| AD1 | 312.0 | 3 |
| AD2 | 349.6 | −8 |
| AD3 | 347.0 | −8 |
| AD4 | 128.6 | 60 |
| AD5 | 300.0 | 7 |
| AD6 | 382.0 | −18 |
| AD7 | 196.0 | 39 |
| AD8 | 94.5 | 71 |

TABLE 2

Efficacy of Allergen Denaturant Solutions on Dog Allergen

| Allergen Denaturant Solution | Can f 1 (μg/ml) | % Reduction Can f 1 |
|---|---|---|
| PBS Control | 149.5 | |
| AD1 | 128.0 | 14 |
| AD2 | 138.0 | 8 |
| AD3 | 72.0 | 52 |
| AD4 | 45.0 | 70 |
| AD5 | 71.2 | 52 |
| AD6 | 145.6 | 3 |
| AD7 | 49.3 | 67 |
| AD8 | 2.2 | 99 |

TABLE 3

Efficacy of Allergen Denaturant Solutions on Cockroach Allergen

| Allergen Denaturant Solution | Bla g 2 (μg/ml) | % Reduction Bla g 2 |
|---|---|---|
| PBS Control | 555.9 | |
| AD1 | 47.8 | 91 |
| AD2 | 59.7 | 89 |
| AD3 | 125.3 | 77 |
| AD4 | 101.0 | 82 |
| AD5 | 272.3 | 51 |
| AD6 | 433.0 | 22 |
| AD7 | 252.3 | 55 |
| AD8 | 144.5 | 74 |

The Allergen Denaturant solutions had significant effect on the Der p 2 mite allergen, Can f 1 dog allergen and Bla g 2 cockroach allergen compared to the PBS Control. Moreover, AD4 and AD8 had a greater effect on the various antigens than the other enzyme solutions, except for AD 1 & AD2 with respect to the cockroach antigen.

Example 4

Efficacy of Allergen Denaturant on Mold Allergens

Three different Allergen Denaturant solutions were prepared using three different subtilisin-type proteases and UNIBOND 1808 (AD9-AD11). Each solution was tested against a standard to ensure that the Allergen Denaturant solutions did not interfere with commercially available mAb ELISA tests (INDOOR Biotechnologies, Inc., Charlottesville, Va.) used to measure exposure to allergens. Detection was performed by using a POWERWAVE 200 (Biotek Instruments, Inc., Winooski, Vt.). The test showed that the Allergen Denaturant solutions did not interfere with the ELISA system.

The Allergen Denaturant solutions were then tested with Asp f1 and Alt a 1 mold allergens. First, the ELISA plates were coated with anti-Asp f 1 mAb 4A6 and anti-Alt a 1 mAb 121 overnight at 4° C. The two allergens were incubated with the six Allergen Denaturant solutions and a PBS control, for a total of 8 samples, and incubated for two hours at room temperature.

After incubation, the samples were diluted 1/100, 1/200, 1/400 and 1/800 and tested with the commercial ELISA kits and detected as described above. Curves of the four dilutions for each sample were generated and compared to the standard curve. An average of the 4 dilutions, as determined by the standard curve, was calculated to determine the concentration of allergen remaining after exposure to the Allergen Denaturant solutions. The effect of the Allergen Denaturant solutions were expressed as a percent reduction of the allergen concentration after exposure to the solutions compared to the concentration of the allergen without an Allergen Denaturant solution (PBS Control). Results of the tests are shown below in Tables 4 an 5 below.

TABLE 4

Efficacy of Allergen Denaturant Solutions on Asp f 1 Mold Allergen

| Allergen Denaturant Solution | Asp f 1 (µg/ml) | % Reduction Asp f 1 |
|---|---|---|
| PBS Control | 149.9 | |
| AD9 | 100.3 | 33 |
| AD10 | 91.4 | 39 |
| AD11 | 135.6 | 10 |

TABLE 5

Efficacy of Allergen Denaturant Solutions on Alt a 1 Mold Allergen

| Allergen Denaturant Solution | Alt a 1 (µg/ml) | % Reduction Alt a 1 |
|---|---|---|
| PBS Control | 231.8 | |
| AD9 | 143.3 | 38 |
| AD10 | 151.2 | 35 |
| AD11 | 77.3 | 67 |

The Allergen Denaturant solutions had moderate effects on the Asp f 1 and Alt a 1 mold allergens, with AD11 having the greatest effect on Alt a 1.

Although the foregoing invention has been described in some detail by way of illustration and example for purposes of clarity of understanding, it will be obvious that certain changes and modifications may be practiced within the scope of the appended claims. Modifications of the above-described modes for carrying out the invention that are obvious to persons of skill in medicine, veterinary medicine, allergy & immunology, entomology, enzymology, pharmacology, and/or related fields are intended to be within the scope of the following claims.

All publications and patent applications mentioned in this specification are indicative of the level of skill of those skilled in the art to which this invention pertains. All such publications and patent applications are herein incorporated by reference to the same extent as if each individual publication or patent application was specifically and individually indicated to be incorporated by reference.

The invention claimed is:

1. A method for reducing allergenicity in ambient air of an indoor space in need thereof, said ambient air having at least one positively charged airborne allergen and said indoor space having allergen reservoirs, said at least one positively charged airborne allergen having polypeptide structures that render the at least one positively charged airborne allergen allergenic, said at least one positively charged airborne allergen selected from the group consisting of house dust mite fecal antigens, cockroach fecal antigens, cat dander, dog dander, mold spores, and combinations thereof, the method comprising:
   a. aerosolizing a negatively charged polyester into ambient air of an indoor space in a manner that completely fills the indoor space with the aerosolized polyester;
   b. the aerosolizing polyester staying airborne for a period of time that will allow the aerosolized polyester to attract at least one positively charged airborne allergen and weigh down the at least one positively charged airborne allergen so that the at least one positively charged airborne allergen will settle into an allergen reservoir; and
   c. applying to said allergen reservoir a means for hydrolytically cleaving the at least one positively charged airborne allergen that settled into the allergen reservoir, thereby breaking peptide bonds and the polypeptide structure of the at least one positively charged airborne allergen and reducing the polypeptide to peptide fragments that are less allergenic and more easily removed from the allergen reservoir; and
   d. removing the at least one positively charged hydrolytically cleaved airborne allergen from the allergen reservoir.

2. The method of claim 1, wherein the step of removing comprises physically removing the at least one positively charged hydrolytically cleaved airborne allergen form the allergen reservoirs in the indoor space by hot water washing.

3. The method of claim 2 further comprising a step of: drying the allergen reservoirs after the hot water washing.

4. The method of claim 1 wherein: said aerosolizing is accomplished via a fogger.

5. A method for reducing allergenicity in ambient air of an indoor space in need thereof, said ambient air having at least one positively charged airborne allergen and said indoor space having allergen reservoirs, said at least one positively charged airborne allergen having polypeptide structures that render the at least one positively charged airborne allergen allergenic, said at least one positively charged airborne allergen selected from the group consisting of house dust mite fecal antigens, cockroach fecal antigens, cat dander, dog dander, mold spores, and combinations thereof, the method comprising:
   a. aerosolizing a negatively charged polyester via a fogger into ambient air of an indoor space in a manner that completely fills the indoor space with the aerosolized polyester;

b. the aerosolizing polyester staying airborne for a period of time that will allow the aerosolized polyester to attract at least one positively charged airborne allergen and weigh down the at least one positively charged airborne allergen so that the at least one positively charged airborne allergen will settle into an allergen reservoir; and c. applying to said allergen reservoir a means for hydrolytically cleaving the at least one positively charged airborne allergen that settled into the allergen reservoir, thereby breaking peptide bonds and the polypeptide structure of the at least one positively charged airborne allergen and reducing the polypeptide to peptide fragments that are less allergenic and more easily removed from the allergen reservoir; and d. removing the at least one positively charged hydrolytically cleaved airborne allergen from the allergen reservoir.

6. The method of claim 5, wherein the step of removing comprises physically removing the at least one positively charged airborne allergen from the allergen reservoirs in the indoor space by hot water washing.

7. The method of claim 6 further comprising a step of: drying the allergen reservoirs after the hot water washing.

8. A method for reducing allergenicity in ambient air of an indoor space in need thereof, said ambient air having at least one positively charged airborne allergen and said indoor space having allergen reservoirs, said at least one positively charged airborne allergen having polypeptide structures that render the at least one positively charged airborne allergen allergenic, said at least one positively charged airborne allergen selected from the group consisting of house dust mite fecal antigens, cockroach fecal antigens, cat dander, dog dander, mold spores, and combinations thereof, the method comprising:

a. aerosolizing a negatively charged polyester via a fogger into ambient air of an indoor space in a manner that completely fills the indoor space with the aerosolized polyester;

b. the aerosolizing polyester staying airborne for a period of time that will allow the aerosolized polyester to attract at least one positively charged airborne allergen and weigh down the at least one positively charged airborne allergen so that the at least one positively charged airborne allergen will settle into an allergen reservoir; and c. applying to said allergen reservoir a means for hydrolytically cleaving the at least one positively charged airborne allergen that settled into the allergen reservoir, thereby breaking peptide bonds and the polypeptide structure of the at least one positively charged airborne allergen and reducing the polypeptide to peptide fragments that are less allergenic and more easily removed from the allergen reservoir; and d. physically removing the at least one positively charged hydrolytically cleaved airborne allergen from the allergen reservoirs in the indoor space by hot water washing; and e. drying the allergen reservoirs after the hot water washing.

* * * * *